United States Patent [19]

Baumann et al.

[11] 4,116,982

[45] Sep. 26, 1978

[54] 3-OXIMINO-4-OXO-2,5-DIMETHYL-TETRAHYDROFURAN

[75] Inventors: Manfred Baumann, Mannheim; Werner Hoffmann, Neuhofen; Karl von Fraunberg, Bobenheim, all of Fed. Rep. of Germany

[73] Assignee: BASF Aktiengesellschaft, Ludwigshafen, Fed. Rep. of Germany

[21] Appl. No.: 811,461

[22] Filed: Jun. 30, 1977

[51] Int. Cl.$^2$ .................................. C07D 307/32
[52] U.S. Cl. ........................... 260/347.7; 426/536
[58] Field of Search .................... 260/347.7; 426/536

[56] References Cited

U.S. PATENT DOCUMENTS

| 3,403,178 | 9/1968 | Völker et al. | 260/347.7 X |
| 3,887,589 | 6/1975 | Eykelboom et al. | 426/536 X |

*Primary Examiner*—Richard L. Raymond
*Attorney, Agent, or Firm*—Keil, Thompson & Shurtleff

[57] ABSTRACT

The new product 3-oximino-4-oxo-2,5-dimethyl-tetrahydrofuran is manufactured by oximation of the new product 3-carboxy-4-oxo-2,5-dimethyl-tetrahydrofuran with aqueous nitrous acid, nitrite esters or nitrosyl chloride. Because of its fine caramel-like fragrance it may be used for the manufacture of scents and flavor materials. In addition it presents an advantageous method of synthesis of the sought-after flavor material 4-oxo-3-hydroxy-2,5-dimethyl-4,5-dihydrofuran (furaneol).

1 Claim, No Drawings

3-OXIMINO-4-OXO-2,5-DIMETHYL-TETRAHYDROFURAN

The present invention relates to 3-oximino-4-oxo-2,5-dimethyltetrahydrofuran, ie. a compound of the formula I

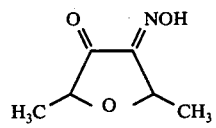

its manufacture by oximation of the new 3-carboxy-4-oxo-2,5-dimethyl-tetrahydrofuran and its use as a scent, as well as its use for the manufacture of the sought-after flavor material 4-oxo-3-hydroxy-2,5-dimethyl-4,5-dihydrofuran.

The new 3-oximino-4-oxo-2,5-dimethyl-tetrahydrofuran has a fine caramel-like fragrance which is very similar to, but slightly weaker than, that of the sought-after scent and flavor material 4-oxo-3-hydroxy-2,5-dimethyl-4,5-dihydrofuran. Because of its interesting olfactory properties, the compound is useful for the manufacture of scents and, preferably, flavor material for a great diversity of applications.

The new compound is also an interesting intermediate for the manufacture of the sought-after 4-oxo-3-hydroxy-2,5-dimethyl-4,5-dihydrofuran, by a new advantageous method of synthesis.

The invention further relates to a process for the manufacture of 3-oximino-4-oxo-2,5-dimethyl-tetrahydrofuran, in which the new 3-carboxy-4-oxo-2,5-dimethyl-tetrahydrofuran is oximated with aqueous nitrous acid, nitrite esters or nitrosyl chloride, preferably with aqueous nitrous acid at from $-50°$ to $+50°$ C.

The new 3-carboxy-4-oxo-2,5-dimethyl-tetrahydrofuran, required as a starting compound for this process, can be prepared in the conventional manner by hydrolyzing the corresponding new alkyl esters under mild conditions by means of $NaHCO_3$, $NaCO_3$, NaOH, KOH or the like, in aqueous solution or suspension, and then acidifying and concentrating the mixture, or, more advantageously, by hydrogenating the corresponding benzyl ester in the presence of noble metal catalysts, eg. Pd or Pt on carriers, eg. C, $CaCO_3$, $SiO_2$ or $Al_2O_3$. The corresponding new alkyl esters (3-carbalkoxy-4-oxo-2,5-dimethyl-tetrahydrofurans) can in turn be obtained by reacting the corresponding crotonate esters with a lactate ester at from $-20°$ to $120°$ C.

The new 2,5-dimethyl-3-carbobenzyloxy-tetrahydrofuran-4-one can be obtained by reacting benzyl crotonate with a lactate ester at from $-20°$ to $120°$ C, or by reacting 2,5-dimethyl-3-carbalkoxytetrahydrofuran-4-ones with benzyl alcohol at from $50°$ to $250°$ C, preferably from $150°$ to $200°$ C.

To oximate 3-carboxy-4-oxo-2,5-dimethyl-tetrahydrofuran, the method used is, for example, to dissolve the starting compound in water or in mixtures of water and water-miscible solvents which do not undergo other reactions under the reaction conditions, eg. lower alcohols or dioxane, add an aqueous solution of an alkali metal nitrite slowly to the resulting solution, with intensive cooling, and finally add a dilute aqueous acid whilst cooling.

The course of the reaction can be followed by the elimination of $CO_2$ which occurs

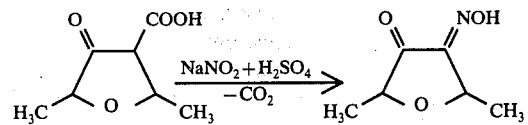

The preferred alkali metal nitrite is $NaNo_2$, which is in general employed in amounts of 1 mole per mole of starting acid.

Examples of suitable aqueous acids are $H_2SO_4$, HCL, $CH_3COOH$ and HCOOH, preferably about half-concentrated (ie. about 50% strength) $H_2SO_4$. In general, from 0.5 to 1 mole of acid is used per mole of nitrite.

The reaction temperature is from about $-50°$ to $+50°$ C, preferably from $0°$ to $10°$ C. The heat of the reaction must be removed by cooling with ice, ice water or brine.

However, the oximation of 3-carboxy-4-oxo-2,5-dimethyl-tetrahydrofuran can also be effected with nitrosyl chloride or with nitrite esters. To carry out the oximation with nitrite esters, the starting acid is dissolved in a solvent, preferably an alcohol and in particular the same alcohol as is present as the alcohol component in the nitrite ester, the ester, eg. methyl nitrite, ethyl nitrite, butyl nitrite, isoamyl nitrite or isobutyl nitrite, is added to this solution and a stream of HCl is slowly passed into the resulting reaction mixture whilst cooling with ice water or with ice.

The reaction in general takes place at from $-50°$ to $+50°$, preferably from $0°$ to $10°$ C.

The oximation batches are worked up in the conventional manner by extraction with a suitable water-immiscible or only slightly water-miscible solvent, eg. petroleum ether, ethyl acetate, $CH_2Cl_2$, $CHCl_3$ or diethyl ether, especially the last-mentioned (the extraction being carried out, if appropriate after first distilling off the solvent used during the oximation), and washing, drying and concentrating the extracts. The oxime is thus obtained in a very pure form in which it can be employed for the manufacture of 4-oxo-3-hydroxy-2,5-dimethyl-4,5-dihydrofuran. Further details of the oximation reaction may be found in Houben-Weyl, "Methoden der Organischen Chemie", 4th edition, 10/4, pages 40–41.

The reaction to give 4-oxo-3-hydroxy-2,5-dimethyl-4,5-dihydrofuran may be carried out by, for example, hydrolysis with aqueous acids, treatment with oxidizing agents or trans-oximation with a reactive carbonyl compound.

The hydrolysis with aqueous acids is in most cases carried out with dilute HCl or $H_2SO_4$, but can also be carried out with organic acids, eg. acetic acid or oxalic acid; advantageously, the reaction mixture, with or without addition of a solubilizing agent, eg. alcohol or acetic acid, is heated at from about $50°$ to $100°$ C. The 4-oxo-3-hydroxy-2,5-dimethyl-4,5-dihydrofuran is isolated in the conventional manner by extracting it by shaking with a suitable solvent.

The oxime I can also be split by treatment with nitrous acid ($NaNO_2$ + acids, eg. NCl, $H_2SO_4$ or $CH_3COOH$) or with other oxidizing agents, eg. nitrite esters + acids, nitrosyl chloride or nitrosyl-sulfuric acid. From 1 to 2 moles of the oxidizing agent are employed, at from about $0°$ to $100°$ C, preferably from $20°$ to $50°$ C. Examples of suitable solvents are water, lower alcohols, acetate esters or excess $CH_3COOH$.

The conversion of 4-oxo-3-carboxy-2,5-dimethyl-tetrahydrofuran to 4-oxo-3-hydroxy-2,5-dimethyl-4,5-dihydrofuran can also be carried out in a single reaction vessel without isolating 3-oximino-4-oxo-2,5-dimethyl-tetrahydrofuran. In that case, the aqueous solution of the crude oxime, obtained from the oximation reaction, is employed directly for the scission of the oxime.

For the trans-oximation of the 3-oximino-4-oxo-2,5-dimethyl-tetrahydrofuran of the invention with a reactive carbonyl compound, formaldehyde is used preferentially. The oxime is heated with about 40% strength aqueous formaldehyde in the presence of hydrochloric acid or sulfuric acid and the reaction mixture is allowed to finish reacting at room temperature or in the cold.

The new 3-oximino-4-oxo-2,5-dimethyl-tetrahydrofuran has a fine fragrance which is very similar to, but slightly fainter than, that of the sought-after flavor material 4-oxo-3-hydroxy-2,5-dimethyl-4,5-dihydrofuran and is therefore very suitable for the manufacture of scents and flavor materials for a great variety of applications. The new compound furthermore offers a new, industrially interesting and advantageous method of synthesis of the above 4-oxo-3-hydroxy-2,5-dimethyl-4,5-dihydrofuran.

EXAMPLE 1 a. 40 g of 4-oxo-2,5-dimethyl-3-carboethoxytetrahydrofuran in 200 ml of benzyl alcohol are heated at 180°–200° C. The methanol formed is distilled off. The excess benzyl alcohol is distilled off under reduced pressure and the residue is fractionated. 45 g (corresponding to 78% of theory) of 4-oxo-2,5-dimethyl-3-carbobenzyloxytetrahydrofuran of boiling point 102° C/0.02 mm Hg and refractive index $n_D^{25}$ = 1.5070 are obtained.

b. 20 g of the benzyl ester obtained as described in 1a are hydrogenated in 100 ml od ethyl acetate with 1 g of 10% strength Pd on charcoal, under normal pressure. 2,280 ml of $H_2$ are taken up. After distilling off the solvent under reduced pressure, 3-carboxy-4-oxo-2,5-dimethyl-tetrahydrofuran is obtained as a colorless oil which solidifies to crystals of melting point 55°–57° C, and the spectroscopic data of which confirm the structure. The yield is quantitative.

c. 60 g of 4-oxo-3-carboxy-2,5-dimethyl-tetrahyrofuran are dissolved in 100 ml of water. A solution of 26 g of $NaNO_2$ in about 50 ml of water is slowly added dropwise thereto at from 0° to 10° C, whilst cooling with ice. Vigorous elimination of $CO_2$ occurs and the contents of the flask turn yellowish.

After adding about half the solution, the evolution of gas ceases. When all the $NaNO_2$ has been added, about 40 ml of 50% strength $H_2SO_4$ are slowly added dropwise at from 0° to 10° C. $CO_2$ is again eliminated. Toward the end of the addition, the evolution of gas subsides and the pH is then about 2–3. The reaction mixture is stirred for a further hour and is then neutralized with NaOH solution and extracted repeatedly with ether, and the ether phase is dried and concentrated. 42 g of 4-oxo-3-oximino-2,5-dimethyl-tetrahydrofuran remain in the form of a pale yellow oil, the spectroscopic data and analysis of which confirm the stated structure. The crude yield is 78% of theory. A sample was distilled under reduced pressure; at the boiling point of 90° C/0.5 mm Hg, partial decomposition takes place.

EXAMPLE 2

15.8 g of 4-oxo-3-carboxy-2,5-dimethyl-tetrahydrofuran are dissolved in 80 ml of ethanol and 15 g of ethyl nitrate are added. A slow stream of HCl is passed in whilst cooling with ice. On warming to 20° C, evolution of gas occurs, accompanied by a slight exothermicity. When evolution of gas has ceased (which is the case after about 1 hour), the mixture is concentrated, the residue is taken up in ether and the ether solution is washed neutral with aqueous $NaHCO_3$ solution, dried and concentrated under reduced pressure. 13.5 g of 4-oxo-3-oximino-2,5-dimethyl-tetrahydrofuran (corresponding to a crude yield of 94% of theory) remain.

EXAMPLE 3

Scission of the oxime I with aqueous acids 10 g of 4-oxo-3-oximino-2,5-dimethyl-tetrahydrofuran and 50 ml of 10% strength $H_2SO_4$ are heated at 80° C and the hydrolysis is followed by thin layer chromatography. The oxime has been converted after 3 hours. In its place, 4-oxo-3-hydroxy-2,5-dimethyl-4,5-dihydrofuran has been formed, as established by isolating the product and comparing the chromatographic and spectroscopic data with those of a comparative substance.

EXAMPLE 4

Scission of the oxime I by trans-oximation with reactive carbonyl compounds 10 g of 4-oxo-3-oximino-2,5-dimethyl-tetrahydrofuran are stirred with 50 ml of a 40% strength formaldehyde solution and 30 ml of 20% strength sulfuric acid for 24 hours at room temperature. Subsequent examination by thin layer chromatography shows that the oxime has been completely converted to 4-oxo-3-hydroxy-2,5-dimethyl-4,5-dihydrofuran.

EXAMPLE 5

Oxidative scission of oxime I a. 40 g of the crude 4-oxo-3-oximino-2,5-dimethyl-tetrahydrofuran obtained as described in Example 1 are suspended in 100 ml of 30% strength $H_2SO_4$ and a solution of 20 g of $NaNO_2$ in 50 ml of water is slowly added dropwise to this suspension at room temperature. A vigorous evolution of gas occurs and the temperature rises; it is kept at 40° C by cooling with ice water. After completion of the dropwise addition, the reaction mixture is allowed to continue reacting for 60 minutes at room temperature and the solution is then neutralized with aqueous NaOH. Thereafter it is extracted with ether and the extract is dried and concentrated. 19.8 g of 4-oxo-3-hydroxy-2,5-dimethyl-4,5-dihydrofuran are left in the form of a yellow oil which, according to analysis by thin layer chromatography, still contains traces of impurities. The yield is 55% of theory.

The further purification of the end product can be carried out by distillation, or by recrystallizing the viscous oil from ether. In the latter case, a colorless substance of melting point 79°–80° C is obtained.

b. A solution of 20 g of $NaNO_2$ in 50 ml of water is added to 40 g of the crude 4-oxo-3-oximino-2,5-dimethyl-tetrahydrofuran obtained as described in Example 1. 100 ml of 30% strength $H_2SO_4$ are added dropwise to this suspension whilst cooling at about 40° C. On working up the reaction batch by the method described in (5a), about the same result is obtained.
We claim:
1. 3-Oximino-4-oxo-2,5-dimethyl-tetrahydrofuran of the formula
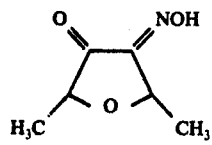
* * * * *

UNITED STATES PATENT AND TRADEMARK OFFICE
CERTIFICATE OF CORRECTION

PATENT NO. : 4,116,982
DATED : Sept. 26, 1978
INVENTOR(S) : BAUMANN ET AL

It is certified that error appears in the above-identified patent and that said Letters Patent are hereby corrected as shown below:

In the Heading after section "[22] Filed: Jun. 30, 1977" insert the following section:

--[30] Foreign Application Priority Data

Jul. 27, 1976  Fed. Rep. of Germany . . 2633663--.

Signed and Sealed this

Tenth Day of April 1979

[SEAL]

Attest:

RUTH C. MASON
Attesting Officer

DONALD W. BANNER
Commissioner of Patents and Trademarks